United States Patent [19]
Esch et al.

[11] Patent Number: 5,187,309
[45] Date of Patent: Feb. 16, 1993

[54] PROCESS FOR THE CONTINUOUS PREPARATION OF LOWER ACRYLATES

[75] Inventors: Marc Esch, Freyming-Merlebach; Nadine Colin, Saint-Avold; Dominique Guenez, Grostenquin; Michel Maraval, Pont-Saint-Maxence, all of France

[73] Assignee: Elf Atochem S.A., Paris, France

[21] Appl. No.: 690,911

[22] PCT Filed: Jul. 6, 1990

[86] PCT No.: PCT/FR90/00516

§ 371 Date: Nov. 29, 1991

§ 102(e) Date: Nov. 29, 1991

[87] PCT Pub. No.: WO91/01966

PCT Pub. Date: Feb. 21, 1991

[30] Foreign Application Priority Data

Aug. 3, 1989 [FR] France .............................. 89/10483

[51] Int. Cl.$^5$ .............................................. C07C 17/48
[52] U.S. Cl. ...................................... 560/218; 560/205
[58] Field of Search ........................... 560/218; 180/205

[56] References Cited

U.S. PATENT DOCUMENTS

| | | | |
|---|---|---|---|
| 2,582,299 | 1/1952 | Vaughan | 560/218 |
| 2,649,475 | 8/1953 | Bellringer | 560/218 |
| 3,431,181 | 3/1960 | Bouniot | 560/218 |
| 3,476,798 | 11/1969 | Kanstle | 560/218 |
| 4,250,328 | 2/1981 | Fujita | 560/205 |
| 4,317,926 | 3/1982 | Sato | 562/532 |
| 4,435,594 | 3/1984 | Matsumura | 560/218 |
| 4,518,462 | 5/1985 | Aoshima | 560/218 |
| 5,028,735 | 7/1991 | Segawa | 560/218 |
| 5,034,558 | 7/1991 | Yoshioka | 560/218 |

FOREIGN PATENT DOCUMENTS

| | | |
|---|---|---|
| 8008042 | 1/1983 | Japan . |
| 8203940 | 11/1983 | Japan . |
| 2099345 | 5/1987 | Japan . |
| 2123150 | 6/1987 | Japan . |
| 2-017150 | 1/1990 | Japan . |

*Primary Examiner*—Paul J. Killos
*Attorney, Agent, or Firm*—Millen, White, Zelano and Branigan

[57] ABSTRACT

Process for the continuous preparation of lower acrylates from an aqueous solution of acrylic acid and from a lower alcohol, the esterification reaction taking place in liquid phase in a reactor, at a temperature of between 50° C. and 110° C., in the presence of at least one esterification catalyst, the reaction products leaving the reactor, consisting of a mixture of lower acrylate, water and unreacted starting compounds, being sent to the bottom of a distillation column and the lower acrylate being recovered at the head of the said column and sent towards a purification device. The said aqueous solution of acrylic acid is introduced at the bottom of the said distillation column where it is subjected to an azeotropic distillation, the stream obtained at the foot of the column, enriched in acrylic acid, then being recycled towards the reactor so that at the entry of the said reactor the molar ratio of acrylic acid to the lower alcohol is between 0.5 and 4.5.

11 Claims, 1 Drawing Sheet

PROCESS FOR THE CONTINUOUS PREPARATION OF LOWER ACRYLATES

The present invention relates to a process for the continuous preparation of lower acrylates from an aqueous solution of acrylic acid and a lower alcohol. More particularly, the present invention relates to a process according to which the reaction of esterification of an aqueous solution of acrylic acid with methanol or ethanol is carried out in liquid phase so as to prepare continuously methyl or ethyl esters of acrylic acid.

It is generally known to prepare the lower (methyl or ethyl) acrylates by esterification of purified acrylic acid with a lower alcohol. It is therefore necessary, in a first operation, to purify the aqueous solution of acrylic acid which is available initially and which assays at at least 50% of pure acrylic acid diluted in a large quantity of water (not more than 50%) and which generally additionally contains lower proportions of impurities which are inherent in its production, including especially acetic acid and aldehydes. The presence of water in the acrylic acid is, in fact, a feature which is unfavourable for obtaining a good conversion when the acid is esterified, because it decreases the formation of the ester by shifting the reaction equilibrium towards the hydrolysis; the acrylic acid conversion would then be so low that it would require major and costly multiple recycling of the unconverted acid and alcohol. A conventional method for purifying the aqueous solution of acrylic acid consists, for example, in carrying out an extractive azeotropic distillation thereon, methyl isobutyl ketone being, for example, an azeotropic solvent which can be employed. After this aqueous solution of acrylic acid has been treated in a purification plant, a purified acrylic acid is generally obtained, assaying at at least 98% of pure acrylic acid, containing a small quantity of water and being consequently capable of being used as a starting material for the esterification reaction. In a second stage, therefore, this purified acrylic acid is introduced directly into an esterification reactor which is simultaneously fed with a lower alcohol (methanol or ethanol). The esterification reaction takes place at a temperature of approximately between 50° C. and 110° C. in the presence of at least one esterification catalyst and at a pressure equal to atmospheric pressure or slightly higher. The reaction products leaving the reactor, consisting of a mixture of lower acrylate, water and unreacted starting compounds, are then sent to the bottom of a distillation column; at the foot of the said column is recovered a mixture of acrylic acid, water and heavy impurities originating from the production of acrylic acid and/or from the esterification reaction, this stream then being recycled towards the esterification reactor in order to feed the said reactor with starting material for the esterification reaction, in addition to the acrylic acid stream originating from the purification device. A mixture consisting of lower acrylate, water and alcohol is recovered at the head of the said column and is then sent towards a purification device comprising, in a first stage, washing with water in order to separate the acrylate from the unreacted alcohol, followed by a distillation of the resulting aqueous phase, this being in order to recover the alcohol which will subsequently be recycled to the reaction, as well as a distillation of the resulting organic phase, this latter distillation making it possible, in a first step, to remove the light impurities and then, in a second step, to remove the residual heavy impurities, finally ending in the production of an acrylate solution assaying at at least 99% of pure acrylate.

The disadvantage of this method lies in the need to provide a purification unit comprising costly and bulky pieces of equipment.

The problem which the present invention proposes to solve consists, therefore, in developing a process which does not have the above disadvantages and which makes it possible to prepare methyl acrylate or ethyl acrylate continuously without resorting to a specific device for purifying the aqueous solution of acrylic acid.

DESCRIPTION OF THE FIGURE

This objective is attained according to the present invention by virtue of a new process, described with reference to FIG. 1, which is appended, permitting the continuous preparation of lower acrylates from an aqueous solution of acrylic acid and from a lower alcohol, the esterification reaction taking place in liquid phase in a reactor 4, at a temperature of approximately between 50° C. and 110° C., in the presence of at least one esterification catalyst, the reaction products leaving the reactor 4, consisting of a mixture of lower acrylate, water and unreacted starting compounds, being sent to the bottom of a distillation column 2 and the lower acrylate being recovered at the head of the said distillation column 2 and sent towards a purification device, characterised in that the aqueous solution of acrylic acid is introduced at the bottom of the said distillation column 2 where it is subjected to an azeotropic distillation, the stream obtained at the foot of the column 2, enriched in acrylic acid, then being recycled towards the reactor 4 so that at the entry of the said reactor 4 the molar ratio of acrylic acid to the lower alcohol is approximately between 0.5 and 4.5.

The aqueous solution of acrylic acid from which the lower acrylate is prepared preferably contains from 50 to 70% of pure acrylic acid diluted in a large quantity of water (approximately from 30% to 50%) and containing lower proportions of impurities which are inherent in its production. The originality of the process according to the invention is based on the fact that the aqueous solution of acrylic acid is no longer purified in a specific purification plant before being introduced into the esterification reactor, but that it is introduced directly, by means of a pipe connection 1, at the bottom of the distillation column 2 used to separate the reaction products leaving the esterification reactor 4, and this offers the advantage of doing away with the use of azeotropic solvents such as, for example, methyl isobutyl ketone.

Figure 1:
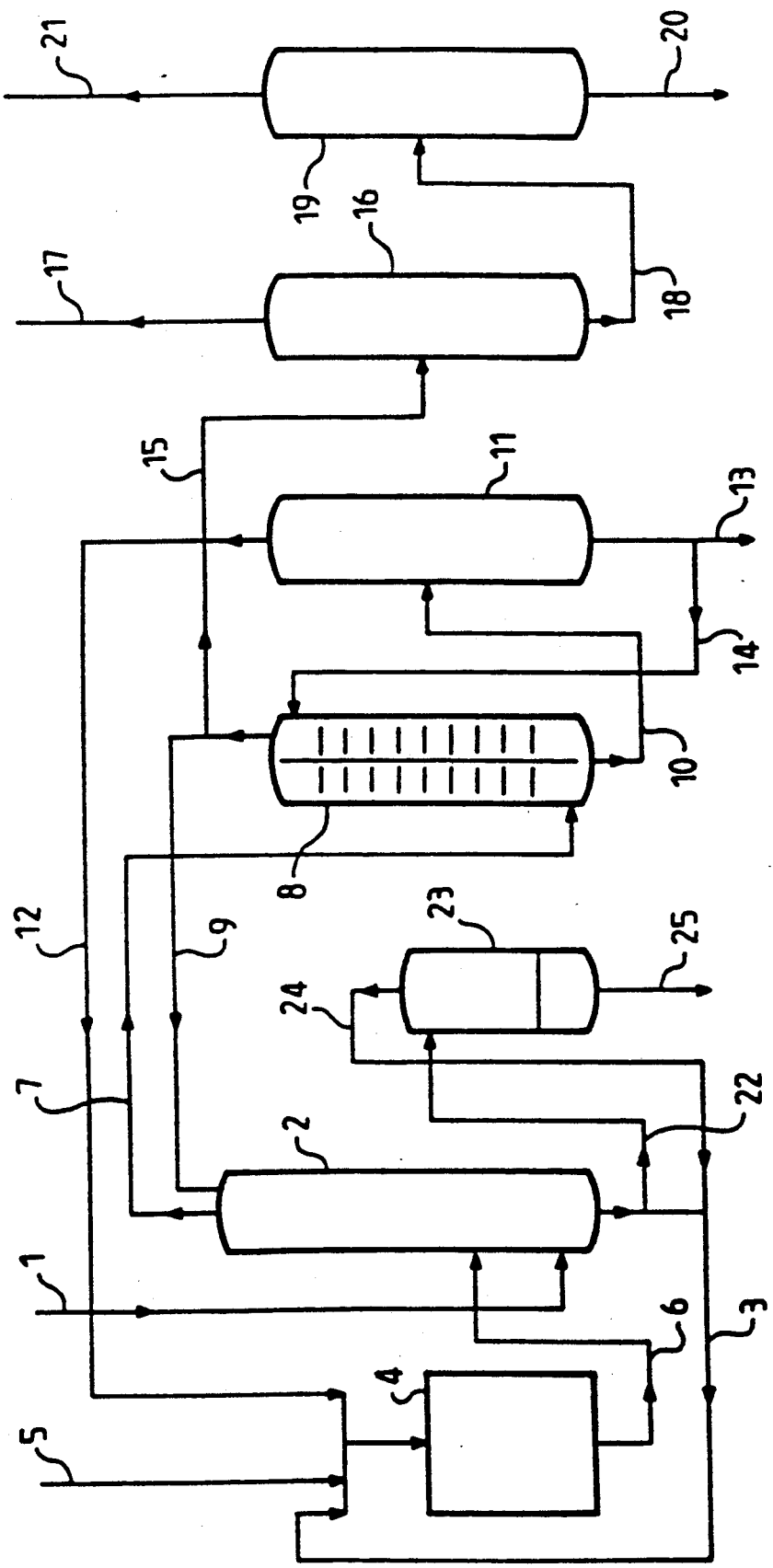

The starting alcohol (methanol or ethanol) which is introduced directly into the esterification reactor 4 by means of a pipe connection 5 is a product which may contain a certain quantity of water; it will be referred to by the term of "fresh alcohol", this being in distinction from the recycled alcohol originating from the section for purifying the reaction products leaving the reactor, and which, for its part, is introduced into the reactor 4 by means of a pipe connection 12; these two alcohol streams will therefore be used to feed the said reactor with raw material for the esterification reaction. The reaction itself takes place in liquid phase, in at least one esterification reactor 4 which may be especially of tubular type with a stationary bed, at a temperature of approximately between 50° C. and 110° C. and preferably between 80° C. and 100° C.; an excessively high reaction temperature would result in the polymerisation of the acrylic acid, while, conversely, an excessively low temperature would make the reaction rate very low.

The pressure inside the reactor 4 is preferably between 1 bar and 3 bars.

Strongly acidic cationic resins may be employed as esterification catalysts, since they enable satisfactory results to be obtained.

In addition, the esterification reaction will be preferably carried out in the presence of at least one polymerisation inhibitor, this being in order to palliate a possible polymerisation of the acrylic acid; inhibitors which are usually employed, such as, for example, hydroquinone or hydroquinone monoethyl ether, may be mentioned as an inhibitor which is perfectly suitable within the scope of the present invention.

The residence time of the products in the reactor 4 is preferably approximately between 1 hour and 5 hours.

The reaction products leaving the esterification reactor 4 are sent, by means of a pipe connection 6, to the bottom of a distillation column 2 comprising at least 5 trays. The latter is therefore intended to receive, on the one hand, the aqueous solution of acrylic acid and, on the other hand, the reaction products leaving the reactor, which consist of a mixture of lower acrylate, water, unreacted starting compounds and a certain number of impurities originating either from the acrylic acid synthesis or from the ester synthesis.

The products present in the said distillation column 2 are subjected to an azeotropic distillation based on the formation of light, water/lower acrylate and water/alcohol, azeotropes, thus making it possible to concentrate the heavy compounds including especially acrylic acid at the bottom of the column and to recover at the head of the column a mixture consisting of light compounds including especially the lower acrylate, alcohol and water. The head temperature of the said column 2 is preferably approximately between 60° C. and 95° C.; the exhaustion of the light compounds, and therefore the reaction conversion and the formation of the heavy compounds, depend especially on the temperature at the foot, which is approximately between 90° C. and 120° C.

This azeotropic distillation therefore makes it possible, on the one hand, to free the crude ester, that is to say the ester which is obtained directly after the esterification reaction and which has not been subjected to any purification stage, from the acrylic acid which it contains and, on the other hand, to remove the water from the reactor 4, thus promoting the esterification reaction in the latter. In addition, to promote the distillation of water in the said column 2 and to avoid the distillation of the acid, a reflux of washed lower acrylate, that is to say of lower acrylate freed from water and alcohol, must be sent to the head of this column; this reflux of washed lower acrylate originates from a washing column 8 receiving at its base the products distilled at the head of the said column 2, that is to say essentially a mixture consisting of lower acrylate, unreacted alcohol and water originating either from the esterification reaction or from the aqueous solution of acrylic acid fed to the said column 2, and the purpose of which is to wash the lower acrylate, that is to say to free it from a high proportion of the water and of the alcohol which it contains, thus recovering at the head of the said washing column 8 the washed lower acrylate, part of which is refluxed, by means of a pipe connection 9, at the head of the distillation column 2. The reflux ratio of washed lower acrylate sent to the head of the said column 2 to promote the formation of the combined ester/water and alcohol/water azeotropes is adjusted as a function of the quantity of water present in the said column; according to the present invention this ratio will e preferably approximately between 0.2 and 4.

The acrylic acid concentrated at the bottom of the said distillation column 2 assays at approximately 50% by weight of pure acrylic acid and approximately from 8% to 20% by weight of water, the remainder consisting essentially of heavy impurities originating from the production of acrylic acid or from the esterification reaction; part of this stream is delivered to the reactor 4 by means of a pipe connection 3, the remainder being conveyed, by means of a pipe connection 22, towards a plant comprising a separating column 23 and an evaporator, in the usual meaning of the term, the heavy by-products being removed at the bottom of the evaporator by means of a pipe connection 25, and the acrylic acid recovered at the head of the said column 23, freed from its heavy impurities, being delivered to the reactor 4 by means of a pipe connection 24 linked to the pipe connection 3. Thus, the acrylic acid used as raw material in the esterification reaction originates solely from the foot of the distillation column 2 and consequently there is not direct feed as far as the esterification reactor 4 is concerned. The recycle ratio which corresponds to the ratio of the flow rate of acrylic acid fed to the distillation column 2, ad which will be referred to as "fresh acrylic acid", to the flow rate of acrylic acid recycled to the reactor 4 by means of the pipe connection 3 is preferably between 0.1 and 0.25.

The acrylic acid stream delivered to the reactor 4 by the pipe connection 3 is such that, at the entry of the said reactor, the molar ratio of acrylic acid to the total lower alcohol introduced into the reactor 4 is approximately between 0.5 and 4.5; however, the fact of operating with excess acid at the entry of the reactor 4 makes it possible to reach a higher reaction temperature, and consequently results in better yields. The total lower alcohol introduced into the reactor 4 means the sum of the recycled alcohol originating from the section for purifying the reaction products and introduced into the said reactor 4 by means of the pipe connection 12, and of the fresh alcohol introduced directly into the said reactor 4 by means of the pipe connection 5. Furthermore, the fresh reactant feed to the plant is such that the molar ratio of fresh acrylic acid to fresh alcohol is will be preferably between 0.5 and 1.

The mixture consisting chiefly of lower acrylate, unreacted alcohol and water, and recovered at the head of the distillation column 2, is sent, by means of a pipe connection 7, to the foot of a washing column 8 used to free the lower acrylate from a high proportion of the water and alcohol which it contains; at the bottom of the said column 8 is recovered a stream consisting of a water-alcohol mixture which is sent, by means of a pipe connection 10, to an alcohol recovery column 11, which allows the alcohol to be separated from the water, the alcohol being recovered at the head of the said column 11 and then recycled to the reactor 4 by means of a pipe connection 12, the water being concentrated at the bottom of the said column 11 to be partly refluxed, by means of a pipe connection 14, at the head of the column 8, the remainder being removed from the plant by means of a pipe connection 13.

At the head of the said washing column 8 is recovered a lower acrylate, washed but still containing reaction byproducts as impurities; part of this washed lower acrylate stream is then refluxed at the head of the distillation column 2, the remaining quantity being delivered, by means of a pipe connection 15, to a separating column 16 which makes it possible to free the acrylate from the light byproducts which it contains, including especially formaldehyde, acrolein, acetone and acetates, the latter being removed at the head of the said column 16 by means of a pipe connection 17. At the foot of the said column 16 is recovered the lower acrylate still containing heavy impurities, including especially maleic acid, acetic acid and the dimers originating from the acrylic acid synthesis, as well as compounds originating from the esterification reaction, such as especially the alkyl alkoxypropionate, the alkyl acryloyloxypropionate and the alkyl maleate, the alkyl group being either a methyl group or an ethyl group; this stream removed at the foot of the column 16 is then delivered, by means of a pipe connection 18, to a separating column 19. At the foot of the said column 19 are recovered the heavy byproducts, which are removed by means of a pipe connection 20, the lower acrylate assaying at at least 99% by weight of pure acrylate being recovered at the head of the said column 19, and then removed by means of a pipe connection 21.

The following nonlimiting examples are given to illustrate the invention better:

EXAMPLE 1

The plant considered is a plant (such as that shown diagrammatically in FIG. 1) for the manufacture of ethyl acrylate obtained by an esterification reaction between an acrylic acid and ethanol in the presence of an esterification catalyst, at a temperature of 80° C. The pressure inside the esterification reactor is 2 bars.

Table I below gives the flow rates of the main material streams in various parts of the plant, together with their composition in percentages by weight. The stream designations are:

F1: the fresh ethanol stream introduced into the reactor 4 by means of the pipe connection 5.
F2: the aqueous solution of acrylic acid delivered to the column 2 by means of the pipe connection 1.
F3: the acrylic acid stream recycled to the reactor 4 by means of a pipe connection 3.
F4: the heavy byproduct stream removed from the evaporator by means of the pipe connection 25.
F5: the distillation product stream leaving at the head of the distillation column 2 and delivered to the separating column 8 by means of the pipe connection 7.
F6: the stream of ethyl acrylate freed from water and alcohol, leaving at the head of the extraction column 8 and recycled at the head of the distillation column 2 by means of the pipe connection 9.
F7: the water stream removed at the bottom of the separating column 11 by means of the pipe connection 13.
F8: the ethanol stream recycled to the reactor 4 by means of the pipe connection 12.
F9: the light byproduct stream removed at the head of the separating column 16 by means of the pipe connection 17.
F10: the pure ethyl acrylate stream obtained at the head of the separating column 19 and removed by means of the pipe connection 21.

The overall yield of the plant, obtained in this illustrative case and expressed in moles of ester produced per mole of acid introduced, is 97.6%.

TABLE I

| Stream | Flow rate in g/h | Composition (% by weight) | | | | | |
|---|---|---|---|---|---|---|---|
| | | Acrylic acid | Ethyl acrylate | Alcohol | Water | Total light compounds | Total heavy compounds |
| F1 | 2,037 | — | — | 94 | 6 | — | — |
| F2 | 5,550 | 58 | — | — | 34 | 2.28 | 5.72 |
| F3 | 22,800 | 45.12 | 1.79 | 3.17 | 16.62 | 1.04 | 32.36 |
| F4 | 200 | 14.7 | 0.8 | 0.6 | 0.5 | — | 83.4 |
| F5 | 22,800 | — | 66.78 | 18.34 | 12.18 | 2.83 | 0.17 |
| F6 | 4,800 | — | 92.35 | — | 2.6 | 4.95 | 0.1 |
| F7 | 1,800 | 2.3 | 0.005 | 0.005 | 97.69 | — | — |
| F8 | 7,875 | — | 14.84 | 74.26 | 8.69 | 2.12 | 0.09 |
| F9 | 260 | — | 42 | 0.37 | 3.2 | 54.43 | — |
| F10 | 4,370 | — | 99.93 | 0.0063 | 0.0027 | 0.061 | — |

EXAMPLE 2

The plant considered is a plant (such as that shown diagrammatically in FIG. 1) for the manufacture of methyl acrylate obtained by an esterification reaction, at a temperature of 85° C., between an acrylic acid and methanol, in the presence of 1.2 liters of resins acting as an esterification catalyst. The residence time of the products inside the reactor is 95 minutes. The head temperature of the distillation column 2 is 64° C., the boiler temperature is 98° C., and the pressure inside the said column 2 is 600 mm Hg ($8 \times 10^4$ Pa).

Table II below gives the flow rates of the main material streams in various parts of the plant, together with their composition in percentages by weight.

The definitions of the streams F1, F2, F3, F5 and F6 are those given in the preceding Example 1.

The overall yield of the test, obtained in this illustrative case and expressed in moles of ester produced per mole of acid introduced, is 98.7%.

TABLE II

| Stream | Flow rate in g/h | Composition (% by weight) | | | | | |
|---|---|---|---|---|---|---|---|
| | | Acrylic acid | Methyl acrylate | Alcohol | Water | Total light compounds | Total heavy compounds |
| F1 | 48.4 | — | — | 100 | — | — | — |
| F2 | 104.0 | 64.89 | — | — | 32.10 | 2.7 | 0.31 |
| F3 | 699 | 63.31 | 0.1 | 0.33 | 18.25 | 1.38 | 16.63 |
| F5 | 647.3 | — | 90.11 | 1.58 | 7.67 | 0.6 | 0.04 |

TABLE II-continued

| Stream | Flow rate in g/h | Composition (% by weight) | | | | | |
|---|---|---|---|---|---|---|---|
| | | Acrylic acid | Methyl acrylate | Alcohol | Water | Total light compounds | Total heavy compounds |
| F6 | 505.9 | — | 99.57 | — | 0.01 | 0.01 | 0.41 |

What is claimed is:

1. Process for the continuous preparation of lower acrylates from an aqueous solution of acrylic acid and from a lower alcohol, the esterification reaction taking place in a liquid phase in a reactor (4), at a temperature of between 50° C. and 110° C., in the presence of at least one esterification catalyst, the reaction products leaving the reactor (4), consisting essentially of a mixture of lower acrylate, water and unreacted starting compounds, being sent to the bottom of a distillation column (2) and the lower acrylate being recovered at the head of the said column (2) and further enriched, characterised in that the aqueous solution of acrylic acid is introduced at the bottom of the said distillation column (2) where it is subjected to an azeotropic distillation, the stream obtained at the foot of the column (2), enriched in acrylic acid, then being recycled towards the reactor (4) so that at the entry of the said reactor (4) the molar ratio of acrylic acid to the lower alcohol is between 0.5 and 4.5.

2. A process according to claim 1, characterised in that the lower acrylate is methyl acrylate on ethyl acrylate and the lower alcohol is methanol or ethanol.

3. A process according to claim 1, characterised in that the aqueous solution of acrylic acid contains from 50 to 70% by weight of pure acrylic acid.

4. A process according to one of claim 1, characterised in that the ratio of enriched lower acrylate refluxed at the head of the column (2) is between 0.2 and 4.

5. A process according to one of claim 1, characterised in that the reactor (4) does not receive an acrylic acid feed other than the stream originating from the foot of the column (2).

6. A process according to one of claim 1, characterised in that the ratio of acrylic acid fed to the column (2) to the acrylic acid recycled to the reactor (4) is between 0.1 and 0.25.

7. A process according to one of claim 1, characterised in that the molar ratio of fresh acrylic acid to the fresh alcohol is between 0.5 and 1.

8. A process according to claim 2, characterized in that the aqueous solution of acrylic acid contains from 50 to 70% by weight of pure acrylic acid.

9. A process according to claim 2, characterized in that the ratio of acrylic acid red to the column (2) to the acrylic acid recycled to the reactor (4) is between 0.1 and 0.25.

10. A process according to claim 8, characterized in that the ratio of acrylic acid fed to the column (2) to the acrylic acid recycled to the reactor (4) is between 0.1 and 0.25.

11. A process according to claim 1, wherein said azeotropic distillation in column (2) being conducted essentially free of azeotropic solvents.

* * * * *